United States Patent [19]

Del Bono et al.

[11] Patent Number: 4,783,447
[45] Date of Patent: Nov. 8, 1988

[54] PROCESS FOR PRODUCING NATURAL HEPARAN SULPHATE AND DERMATAN SULPHATE IN SUBSTANTIALLY PURE FORM, AND THEIR PHARMACEUTICAL USE

[75] Inventors: Rinaldo Del Bono, Milan; Luigi De Ambrosi, Santhia; Piergiuseppe Pagella, Isola S. Antonio; Gianni Ferrari, Milan, all of Italy

[73] Assignee: Mediolanum Farmaceutici Srl, Milan, Italy

[21] Appl. No.: 838,133

[22] Filed: Mar. 10, 1986

[30] Foreign Application Priority Data

Mar. 13, 1985 [IT] Italy ................. 19885 A/85

[51] Int. Cl.$^4$ ..................... A61K 31/725; C08B 37/10
[52] U.S. Cl. ........................................ 514/56; 536/21; 514/822
[58] Field of Search ............. 514/56; 536/21, 55.1, 536/55.2, 55.3

[56] References Cited

U.S. PATENT DOCUMENTS 3,862,003  1/1975  Okuyama et al. .................. 435/274
4,243,582  1/1981  Spilburg et al. .................... 530/395

FOREIGN PATENT DOCUMENTS 0097625  1/1984  European Pat. Off. ............ 536/121

*Primary Examiner*—John W. Rollins
*Attorney, Agent, or Firm*—Stevens, Davis, Miller & Mosher

[57] ABSTRACT

A process for producing natural heparan sulphate and dermatan sulphate for mixtures of proteoglycans from the aorta, myocardium and particularly vascularized organs, based on a series of precipitation and purification steps which enable the protein part of the proteoglycan to be eliminated and the two products to be obtained in substantially pure form, without any chemical or enzymatic degradation.

When administered orally or parenterally, the heparan sulphate obtained exerts activation effects on antithrombin III and on the fibrinolytic process.

The dermatan sulphate obtained exerts an inhibiting effect on Factor Xa and also possesses the property of activating the fibrinolytic effect of heparan sulphate.

12 Claims, No Drawings

PROCESS FOR PRODUCING NATURAL HEPARAN SULPHATE AND DERMATAN SULPHATE IN SUBSTANTIALLY PURE FORM, AND THEIR PHARMACEUTICAL USE

This invention relates to a new process for producing natural heparan sulphate and dermatan sulphate in substantially pure form, and their pharmaceutical use.

More particularly, the invention relates to a process for producing heparan sulphate and dermatan sulphate from mixtures of proteoglycans of animal tissues from the aorta, myocardium and particularly vascularised organs, based on eliminating the protein component of the proteoglycans by mild treatment which enables the structure of the two mucopolysaccharides to be integrally maintained.

This process offers doubtless advantages over processes of the known art in that it enables heparan sulphates and dermatan sulphates to be obtained in a substantially pure form, ie not contaminated with other mucopolysaccharide families, it avoids any chemical or enzymatic degradation of the products themselves, and can also by easily transferred to industrial production.

The mucopolysaccharides, which are widely distributed in the various centers of the body, are constituted by heterogeneous macromolecule complexes, and have structures and pharmacological profiles which differ substantially according to the role which they are called on to perform.

Variations in the structure, and consequently in the pharmacological profile, are often induced by the chemical and enzymatic treatment used for their industrial purification in accordance with known processes.

Heparan sulphate and dermatan sulphate are generally obtained from a mucopolysaccharide mixture constituting a by-product of heparin processing.

The long series of chemical and enzymatic treatment, precipitation, fractionation etc. necessary for recovering the heparins and eliminating their contaminants always leads to a degradation of the heparan sulphate and dermatan sulphate structures with consequent variation in the pharmacological profile, in relation to the fractionation and purification method used.

When operating in accordance with the processes of the known art, the reactions for releasing the mucopolysaccharides are conducted at 55° C. with proteolytic enzymes. Protein coagulation is effected by heating to 100° C. and in addition complexing is carried out with quaternary ammonium salts. Less drastic methods, known in the present state of the art, are particularly difficult and costly and are implemented only in laboratory preparation.

Because of the fact that the mucopolysaccharides situated in the aorta, in the myocardium and in the particularly vascularised organs are delegated to coagulative hemeostasis a process such as that of the present invention, which is suitable for their extraction from said organs while preserving their natural structure unaltered, is of particular importance.

The process according to the present invention avoids reactions for releasing the mucopolysaccharides at 55° C. by means of proteolytic enzymes, it also avoids heating to 100° C. for coagulating the proteins and further avoids complexing by means of quaternary ammonium salts.

Thus in practice, those stages which subject the materials to treatment which denatures the delicate structure of these compounds are avoided.

The process for producing natural heparan sulphate and dermatan sulphate in substantially pure form from mixtures of proteoglycans of animal tissues from the aorta, myocardium and particularly vascularised organs, in accordance with the present invention, comprises the following stages:

extracting the proteoglycans from said tissues in finely micronised form by treatment with a solution of urea or the like;

filtering and clarifying the solution, and eliminating the urea or the like;

splitting the bond between the mucopolysaccharides and proteins;

precipitating the proteins and filtering;

eliminating the nucleic acid traces;

precipitating the mucopolysaccharides;

fractionating the heparan sulphate and dermatan sulphate and purifying them.

These and further characteristics of the process according to the invention, and of the products obtained will be more apparent from the detailed description given hereinafter which relates to preferred methods for implementing the process and to the pharmacological trials.

The process consists of two operational cycles: in a first cycle, starting from the raw material, a crude product is produced constituted by a mixture of mucopolysaccharides; in the second cycle, this is fractionated, and the individual mucopolysaccharides are purified.

The raw materials used in the process consist in swine tissues comprising aorta, myocardium and particularly vascularised organs, which are finely micronized.

Apart a demineralized water solution containing from 0.5 to 2% by weight of sodium acetate, from 0,5 to 1% by weight of sodium salt of EDTA and from 20 to 35 by weight of urea is prepared and in said solution the micronized product is suspended with a ratio of said solution to said micronized product form 2 and 4 by weight.

The obtained suspension is stirred at room temperatura for a period of from 15 to 50 hours with the purpose of obtaining the extraction of the proteoglycans.

Aternatively guanidine, thiourea and potassium thiocyanate can be employed in the place of the urea.

Said suspension is filtered through a rotary filter to give an opalescent liquid which is subjected to ultrafiltration through tubular membranes in order to partially eliminate the urea.

The solution is repeatedly washed with demineralized water, and ultrafiltered until the urea content is less than 5% by weight. This liquid is then treated with a sodium chloride solution at a concentration of between 8.7% and 14.5 by weight, in a quantity such as to obtain a final NaCl concentration of between 1.5 and 2.5M. This treatment, the purpose of which is to split the bond between the mucopolysaccharides and proteins, is conducted under agitation at ambient temperature for a time of between 5 and 15 hours.

The proteins are then precipitated by adding trichloracetic acid at a concentration of between 3% and 6% by weight, and are then separated by filtration in a filter press.

The nucleic acid traces are then eliminated by treatment with diatomaceous earth in a quantity of between 2% and 5% by weight with respect to the solution, at a pH of between 3 and 4, under agitation at ambient temperature for 2 hours.

The solids are separated by filtration in a filter press, the pH is adjusted to between 5 and 6 by adding a NaOH solution, and the mucopolysaccharides are precipitated by adding alcohols or ketones such as methanol, ethanol or acetone, in a volumetric ratio of between 0.8:1 and 1.2:1 with respect to the solution.

On filtration, the crude product is obtained consisting of mucopolysaccharides having the following average composition on a dry basis:
Chondroitin sulphate A: 15% by weight
Dermatan sulphate: 20% by weight
Heparan sulphate: 65% by weight Crude product fractionation and purification of the individual mucopolysaccharides are effected by the following operations.

The crude product is dissolved in demineralised water of a quantity such as to obtain a solution of between 1% and 3% by weight, and the solution thus obtained is treated with cationic resins and then neutralised by adding calcium hydroxide. Acetone is added to obtain the fractional precipitation of the individual mucopolysaccharides in the following manner: at an acetone concentration of 30% by volume, the dermatan sulphate precipitates and is separated by filtration; on further increasing the acetone concentration in the solution up to 50% by volume, the heparan sulphate precipitates.

The two precipitates are each separately redissolved in a 2M sodium chloride solution of a quantity such as to attain a concentration of between 3% and 7% by weight in said solution.

The solutions obtained are clarified by filtration and the respective mucopolysaccharides are precipitated by methanol in a volumetric ratio of between 0.8:2 with respect to the solutions.

The products obtained are finally lyophilized.

The products obtained by the process according to the present invention have the following characteristics:

HEPARAN SULPHATE

Molecular weight: within a range of 5000 to 30,000 daltons (determined by gel filtration against a mucopolysaccharide standard);
Degree of sulphation: average 1.2 $SO_4^=$/hexosamine (determined by gravimetric method);
Degree of iduronation: 30–40% (calculated by the carbazole:orcinol ratio);
Electrophoresis: single band with Rf 1.90–1.96 cm. Method of Cappelletti et al. Analyt. Biochem. (1979) 99, 311—Run times: 1st run=3 min, 2nd run=15 min, 3rd run=20 min.

DERMATAN SULPHATE

Molecular weight: within a range of 20000 to 45000 daltons (determined by gel filtration against a mucopolysaccharide standard);
Degree of sulphation: 1.1–1.2 $SO_4^=$/hexosamine (determined by gravimetric method);
Degree of iduronation: 45–65% (calculated by the carbazole:orcinol ratio);
Electrophoresis: single band with Rf 2.15–2.20 cm. Method of Cappelletti et al. Analyt. Biochem. (1979), 99, 311. Run times: 1st run=3 min, 2nd run=15 min, 3rd run=20 min.

These products, when administered either orally or parenterally to human being affected by thrombogenic forms, show the following main pharmacodynamic characteristics:

HEPARAN SULPHATE absence of anticoagulating activity (hepato-Quick; PTTA);
low activity on factor Xa;
induces activation of antithrombin III;
produces significant fibrinolytic effects (euglobulin lysis under normal conditions and after venous stasis.

DERMATAN SULPHATE low anticoagulating activity (hepato-Quick; PTTA);
inhibiting effect on factor Xa;
induces a lowering of the antithrombin III plasma levels;
significant fibrinolytic effects;
has the property of activating and potentiating the fibrinolytic effects of heparan sulphate.

PHARMACOLOGICAL TRIALS

The pharmacological profile of heparan sulphate and dermatan sulphate obtained by the process of the present invention, and the pharmacological logical interactions between the two substances, were evaluated in vivo on voluntuary patients of both sexes between 45 and 70 years old, affected by thrombogenic illnesses of venous nature (thrombophlebitis, varicophlebitis etc.) and of arterial nature (microangiopathy).

The products were administered both orally and parenterally in a single administration at various dosage levels, and the interactions with the coagulative and fibrinolytic processes were evaluated at various times.

Having noted that the products have qualitatively the same dosedependent pharmacological profile both for parenteral and oral administration, the data given hereinafter are those obtained for the maximum tested intramuscular dose, which best allows characterisation of the interactions between the individual compounds or their association, and the coagulative and fibrinolytic processes.

The trial was conducted using the individual products, namely heparan sulphate and dermatan sulphate, and also an equal-weight association of heparan sulphate with dermatan sulphate.

The association of heparan sulphate with dermatan sulphate was chosen at equal-weight because preliminary tests had shown that this best underlined the positive interactions between the two substances (complementary effects on coagulation, and activation of the fibrinolytic effect of heparan sulphate by the dermatan sulphate).

The administration details and the results obtained are given in the following tables:

TABLE 1

Comparison of the effects of heparan sulphate (HS), dermatan sulphate (DS) and the association (HS + DS 1:1 by weight) on the hepato-Quick time (E-QT), on the partial thromboplastin activation time (PTTA) and on the thrombin time (TT).

| Product | Method of administr. | Dose mg | Maximum variation (*) with respect to base value | | |
|---|---|---|---|---|---|
| | | | T-EQ | PTTA | TT |
| DS | i.m. | 25 | +2.46% (6) | +4.51% (2) | +4.54% (2) |
| HS | i.m. | 25 | +1.32% (6) | +4.01% (4) | +2.23% (4) |
| HS + DS | i.m. | 25 + 25 | −0.25% (2-4) | +5.18% (4) | +3.84% (4) |

Values in parentheses indicate the times, in hours, of maximum activity after administration
(*), (+) increase; (−) reduction

TABLE 2

Comparison of the effects of heparan sulphate (HS), dermatan sulphate (DS) and the association (HS + DS, 1:1 by weight) on Factor Xa and on antithrombin III (AT III).

| Product | Method of Administr. | Dose mg | Maximum variation (*) with respect to base value | |
|---|---|---|---|---|
| | | | Xa | AT III |
| DS | i.m. | 25 | −36.4% (2) | −9.14% (2) |
| HS | i.m. | 25 | −5.14% (4) | +5.82% (6) |
| HS + DS | i.m. | 25 + 25 | −37.05% (2) | zero |

The values in parentheses indicate the times, in hours, of maximum activity after administration
(*), (+) increase; (−) reduction.

TABLE 3

Comparison of the effects of heparan sulphate (HS), dermatan sulphate (DS, and the association (HS + DS, 1:1 by weight) on the plasma contents of fibrinogen (FB), $\alpha_2$-antiplasmin ($\alpha_2$-AP) and plasminogen (PA)

| Product | Method of administr. | Dose mg | Maximum variation (*) with respect to base value | | |
|---|---|---|---|---|---|
| | | | FB | $\alpha_2$-AP | PA |
| DS | i.m. | 25 | −8.8% (6) | −9.3% (6) | −6.2% (6) |
| HS | i.m. | 25 | −17.6% (6) | −17.1% (6) | −20.4% (6) |
| HS + DS | i.m. | 25 + 25 | −21.8% (6) | −23.3% (4) | −31.9% (4) |

The values in parentheses indicate the times, in hours, of maximum activity after administration
(*), (+) increase; (−) reduction.

TABLE 4

Comparison of the effects of heparan sulphate (HS), dermatan sulphate (DS) and the association (HS + DS, 1:1 by weight) on the euglobulin lysis time (ELT) and on the euglobulin lysis time after venous stasis (ELTSTAS)

| Product | Method of administr. | Dose mg | Maximum variation (*) with respect to base value | |
|---|---|---|---|---|
| | | | ELT | ELT-STAS |
| DS | i.m. | 25 | −6.9% (4) | −8.8% (4) |
| HS | i.m. | 25 | −33.7% (4-6) | −30.2% (4-6) |
| HS + DS | i.m. | 25 + 25 | −50.12% (2) | −47.9% (2) |

The values in parentheses indicate the times, in hours, of maximum activity after administration
(*), (+) increase; (−) reduction.

The aforesaid data show that pure heparan sulphate and dermatan sulphate, when obtained in accordance with the process of the present invention in the absence of drastic treatment and thus able to preserve serve the natural structure of the two polysaccharides, possess the following pharmacological properties:

(a) neither heparan sulphate nor dermatan sulphate are able to significantly modify the hepato-Quick time, the partial thromboplastin activation time or the thrombin time. The association of the two compounds behaves in the same manner (Table 1);

(b) dermatan sulphate exerts a significant Factor Xa inhibition; heparan sulphate shows no significant effects; the association has an inhibition value equivalent to that obtained with dermatan sulphate alone (Table 2);

(c) dermatan sulphate administration substantially reduces the plasma antithrombin III content; heparan sulphate increases it although only weekly; the association has no effect (Table 2);

(d) heparan sulphate has a significant fibrinolytic effect, which however is low in the case of dermatan sulphate; the association demonstrates a consistent potentiation of the effect and an anticipation in the time, evidently demonstrating activation induced by the dermatan sulphate compared with the fibrinolytic effect of heparan sulphate itself (Tables 3 and 4).

It can therefore be stated that the heparan sulphate obtained in accordance with the invention possesses essentially fibrinolytic and antithrombin III activation properties without interfering with the pharmacological properties of the dermatan sulphate.

This latter acts significantly in inhibiting Factor Xa (probably via heparin cofactor II activation), without significantly altering the coagulation time, while surprisingly activating the fibrinolytic effects of the heparan sulphate.

Preliminary repeated treatment tests, both oral at doses of between 75 and 600 mg: day and intramuscular at doses of between 50 and 400 mg/day, confirm the above results, and in particular demonstrate not only the absence of significant side-effects but also the presence of the following effects:

in the case of dermatan sulphate alone, significant results in preventing venous thromboses in particular:
in the case of heparan sulphate alone, significant results in the treatment of venous and arterial thrombogenic forms;
in the case of the heparan sulphate/dermatan sulphate association, significant results have been obtained in the prevention and treatment of venous and arterial thrombogenic forms and of atherosclerotic manifestations.

The following example of the preparation of heparan sulphate and dermatan sulphate is given as a non-limiting illustration of the process according to the present invention.

EXAMPLE 1

1000 Kg of aorta, myocardium tissues and considerably vascularised organs of mammal origin are finely micronised and treated for 24 hours under agitation at ambient temperature with a solution formed from 2000 liters of demineralized water, 20 Kg of sodium acetate, 10 Kg of EDTA sodium salt and 700 Kg of urea.

The mixture obtained is filtered through a rotary filter, and the clear liquid is ultrafiltered through tubular membranes and concentrated to about 200 liters.

The liquid is then diluted with 200 liters of demineralised water and is then ultrafiltered and concentrated to 200 liters. This diluition with demineralized water, ultrafiltration and concentration is repeated a further two times in order to obtain a solution with a urea content of less than 5% by weight. Sodium chloride is added to a concentration of 2M, and the mixture kept under agitation for 8 hours at ambient temperature. 40 liters of a 20 weight % trichloroacetic acid solution is added, and the proteins which precipitate are filtered off by means of a filter press.

6 Kg of diatomaceous earth are added, the pH is adjusted to 4, the mixture kept under agitation for 2 hours at ambient temperature, and then filtered by means of a filter press.

The solution pH is adjusted to 5.5 by adding KOH, and like parts by volume of methanol are added to precipitate 0.500 Kg of a mucopolysaccharide mixture having the following average composition:
Chondroitin sulphate A: 13.5% by weight
Dermatan sulphate: 22.0% by weight
Heparan sulphate: 64.6% by weight This mixture is dissolved in demineralized water of a quantity such as to obtain a solution of 2 weight % concentration, which is treated with cationic resins and neutralised with calcium hydroxide, after which acetone is added to a concentration of 30% by volume.

The dermatan sulphate precipitates in this manner, and is recovered by decantation and filtration.

Acetone is further added to the liquid to a concentration of 50% by volume, to precipiate the heparan sulphate which is recovered by decantation and filtration.

The two products are further treated, each separately in the following manner:
they are redissoved in a 2M sodium chloride solution of a quantity such as to obtain 5 weight % solutions of the two products, the solutions are filtered and the two products are reprecipitated by treatment with methanol in a volume ratio of 1:2 with respect to the solution.

The two products are finally lyophilised, to thus obtain 240 g of heparan sulphate and 150 g of dermatan sulphate in lyophilised form.

We claim:

1. A process for producing natural heparan sulphate and dermatan sulphate is substantially pure form from mixtures of proteoglycans of animal tissues from the aorta, myocardium and vascularized organs, characterized by the following stages:
    extracting the proteoglycans from said tissues in finely micronized form by treatment with a solution of a compound selected from the group consisting of urea, quanidine, thiourea and potassium thiocyanate;
    filtering and clarifying the solution, and partially eliminating the solution of a compound selected from the group consisting of urea, quanidine, thiourea and potassium thiocyanate;
    splitting the bond between the mucopolysaccharides and proteins;
    precipitating the proteins and filtering
    eliminating the nucleic acid traces;
    precipitating the mucopolysaccharides;
    fractionating the heparan sulphate and dermatan sulphate and purifying them.

2. A process as claimed in claim 1, characterized in that said proteoglycan extraction is effected by treating said tissues with a solution of demineralized water containing between 0.5% and 2% by weight of sodium acetate, between 0.2% and 1% by weight of EDTA sodium salt, and between 20% and 30% by weight of urea in a weight ratio of solution to tissues which lies between 2 and 4, under agitation, at ambient temperature, for a time of between 15 and 50 hours.

3. A process as claimed in claim 1, characterized in that said elimination of urea quanidine, thiourea, or potassium thiocyanate is effected by repeated dilution with demineralized water and concentration with ultrafiltration, the repetition being continued until a solution is obtained having a content of less than 5% by weight of urea quanidine, thiourea, or potassium thiocyanate.

4. A process as claimed in claim 1, characterized in that said splitting of the bond between mucopolysaccharides and proteins is effected by treating the liquid of the preceding stage with a sodium chloride solution of concentration between 8.7% and 14.5% by weight in a quantity such as to obtain a final NaCl concentration of between 1.5 and 2.5M, at ambient temperature, for a time of between 5 and 15 hours.

5. A process as claimed in claim 1, characterized in that said protein precipitation is effected by treatment with trichloroacetic acid at a concentration of between 3% and 6% by weight.

6. A process as claimed in claim 1, characterized in that said nucleic acid elimination is effected by treatment with diatomaceous earth in a quantity of between 2% and 5% by weight with respect to the solution, at a pH of between 3 and 4, under agitation at ambient temperature for 2 hours.

7. A process as claimed in claim 1, characterized in that said mucopolysaccharide precipitation is effected by treatment with a compound selected from the group consisting of methanol, ethanol and acetone in a volumetric ratio of between 0.8:1 and 1.2:1 with respect to the solution, at a pH of between 5 and 6.

8. A process as claimed in claim 1, characterized in that said fractionation of the heparan sulphates and dermatan sulphates is effected by dissolving the crude product containing them in demineralized water to the extent of 1%–3% by weight, treating with cationic resins, neutralizing with calcium hydroxide and effecting fractional precipitation by adding acetone, firstly up to a concentration of 30% by volume and then up to a concentration of 50% by volume.

9. A process as claimed in claim 1, characterized in that said purification of the heparan sulphates and dermatan sulphates is effected by redissolving the two crude products, each separately, in a 2M sodium chloride solution in a quantity such as to attain a concentration in this solution of between 3% and 7% by weight, filtering, and then reprecipitating the pure products by adding methanol in a volumetric ratio of between 0.8:2 and 1.2:2 with respect to the solution.

10. A therapeutic method of treating thrombogenic, venous, arterial and atherogenic episodes which comprises administrating heparan sulfate, obtained by the process of claim 1, orally in doses of 75–600 mg/day or parenterally in doses of 50–400 mg/day.

11. A therapeutic method of preventing venous thrombosis which comprises, administering dermatan sulfate, obtained by the process of claim 1, orally in doses of 75–600 mg/day or parenterally in doses of 50–400 mg/day.

12. A therapeutic method of treating and preventing thrombogenic, venous arterial and atherogenic episodes which comprises, administering heparan sulphate and dermatan sulphate, obtained by the process of claim 1, in a weight ratio of 1 to 1, orally in doses of 50–600 mg/day or parenterally in doses of 50–400 mg/day.

* * * * *